(12) United States Patent
Burgarella et al.

(10) Patent No.: US 7,214,347 B1
(45) Date of Patent: May 8, 2007

(54) PRINTHEAD MOUNTING SYSTEM FOR A MICROARRAY SPOTTING INSTRUMENT

(75) Inventors: Steven M. Burgarella, Framingham, MA (US); Paul E. Glynn, Braintree, MA (US)

(73) Assignee: PerkinElmer LAS, Inc., Boston, MA (US)

( * ) Notice: Subject to any disclaimer, the term of this patent is extended or adjusted under 35 U.S.C. 154(b) by 426 days.

(21) Appl. No.: 09/815,632

(22) Filed: Mar. 23, 2001

(51) Int. Cl.
*B01L 3/02* (2006.01)
*B41J 2/005* (2006.01)

(52) U.S. Cl. .................. 422/100; 422/63; 422/104; 347/20; 347/40; 346/78

(58) Field of Classification Search ............. 422/62, 422/63, 99, 100, 104; 347/1, 20, 40, 74; 346/78
See application file for complete search history.

(56) References Cited

U.S. PATENT DOCUMENTS

| 4,080,607 A | * | 3/1978 | Van Breemen et al. ........ 347/74 |
| 5,615,958 A | * | 4/1997 | Furrow et al. .............. 400/208 |
| 6,101,946 A | | 8/2000 | Martinsky .................... 101/494 |
| 6,447,723 B1 | * | 9/2002 | Schermer et al. ............. 422/62 |
| 6,594,432 B2 | * | 7/2003 | Chen et al. .................. 385/133 |

OTHER PUBLICATIONS

Yoder, Jr., "Design and Mounting of Prisms and Small Mirrors in Optical Instruments, Copyright 1998 The Society of Photo-Optical Instrumentation Engineers," Tutorial Texts in Optical Engineering, vol. TT32, Chapter 2—Attributes of the Successful Optical-to-Mount Interface pp. 14-18.

* cited by examiner

*Primary Examiner*—Brian R. Gordon
(74) *Attorney, Agent, or Firm*—Wilmer Cutler Pickering Hale and Dorr LLP

(57) ABSTRACT

A microarray spotter printhead is mounted to a bracket with a semi-kinematic mounting system for avoiding the need for calibration when replaced.

15 Claims, 3 Drawing Sheets

PRINTHEAD MOUNTING SYSTEM FOR A MICROARRAY SPOTTING INSTRUMENT

BACKGROUND OF THE INVENTION

This invention relates to a microarray potting instrument ("spotter").

Microarrays are arrays of very small samples of purified DNA or protein target material arranged as a grid of hundreds or thousands of small spots immobilized onto a solid substrate. The samples in the array are exposed to complementary genetic or protein probe samples derived from cells that have been labeled with fluorescent dyes. DNA probe material selectively binds to target spots only where complementary bonding sites occur, through a process called hybridization. Subsequent quantitative scanning in a fluorescent microarray scanner produces a pixel map of fluorescent intensities. This fluorescent intensity map can be analyzed by special purpose quantitation algorithms which reveal the relative concentrations of the fluorescent probes and hence the level of gene expression, protein concentration, etc. present in the cells from which the probe samples were extracted. The microarray spotter can also be used for other protein reactions.

The microarray substrate is generally made of glass that has been treated chemically to provide for molecular attachment of the spot samples of microarray target material. The microarray substrate is also generally of the same size and shape as a standard microscope slide, i.e., about 25 mm×75 mm×1 mm thick. The array area can extend to within about 1.5 mm of the edges of the substrate. The spots of target material (typically DNA or protein) are approximately round. The spot diameter can vary from about 75 microns to about 500 microns, depending on the dispensing or spotting technique used. There is a general trend toward smaller spots and more compact arrays. The center-to-center spacing between the spots typically falls into the range of 1.5 to 2.5 spot diameters.

The microarray target material is typically stored in 96-well or 384-well plates, with each well in each plate holding a unique target sample in the form of a liquid solution. Some number of these plates are loaded into the microarray spotting instrument. The instrument, using various levels of automation, draws a small amount (0.3–15 microliter) of material into a spot dispenser, and then dispenses spots of much smaller amounts (0.3–5 nanoliter) onto multiple microarray substrates. The spotting instrument may be equipped with multiple (4–64) spot dispensers which allow the spotting of several samples to occur in parallel, thereby increasing instrument throughput.

The general process of spotting, regardless of dispenser type, includes causing the spotting instrument to execute a sequence of spotting cycles, each cycle including dipping a dispenser into the liquid sample in the plate well where some amount is taken up by vacuum aspiration, capillary action or surface tension; moving the dispenser to an appropriate spotting location above a microarray substrate and causing the dispenser to dispense material for one spot; moving the dispenser to a next spotting position and dispensing until all of the spots to be printed with that sample have been dispensed; washing the residual sample from the dispense; drying the dispenser; and repeating the above cycle until all of the desired samples have been dispensed.

Microarray target material can be deposited as spots on substrates by several methods, and spotting instruments utilizing all of these spot dispensers are commercially available. One method works in a manner similar to an ink-jet printer, such that a few microliters of sample are aspirated by vacuum out of a plate well into a hollow tube. The tip of this hollow tube is configured as a nozzle. When the nozzle has been placed at an appropriate location above a microarray substrate, the instrument dispenses the material to form one spot by applying a pulse of pressure to the liquid in the dispensing tube. This dispensing pressure pulse is typically generated by either a combination of a static pressure created upstream by a motorized syringe or other pump or by causing near instantaneous boiling and the momentary opening of a solenoid valve, or by a piezo-electric squeezing pulse applied to a glass capillary tube that forms the nozzle. One or more droplets are ejected, striking the substrate and drying to form a microarray target spot. Ink-jet spotting instruments are typically equipped with 4–8 dispensers.

Another major category of microarray spotting dispenser uses pins. Pin-type microarray spotting instruments are more widely used than ink-jet type instruments and have several advantages in the DNA microarray application. First, pins generally are simpler and quicker to clean between spotting cycles. Cleaning should be done quickly and thoroughly to maintain spotting instrument throughput and to minimize the possibility of cross-contamination between samples. Second, it is fairly straightforward to fit a spotting instrument with dozens of pins—16-pin, 32-pin, 48-pin, and 64-pin printheads are currently commercially available. Ink-jet dispensers are generally limited to about 8 per instrument due to their complexity, so a pin-type instrument fitted with many pins can have an advantage in increased microarray throughput. Third, most types of pins are less expensive and require fewer instrument control features than ink-jet microarray spotter dispensers. Ink-jet dispensers are advantageous, however, for spotting viscous or thick microarray target samples, such as proteins, and in applications where the precise volume of liquid dispensed to each spot must be controlled.

Microarray spotting pins have been developed and are commercially available in several distinct forms. The pins can be solid, typically with a shaft diameter of about 1 mm and a tapered point with a small flat on the tip. An area of the flat on the tip (along with the surface properties of the sample liquid and the microarray substrate) determines the size of the spot that the pin forms. Solid pins are simple and robust, but in being dipped into the target material in the well only take up enough material to form one spot. This limitation requires the spotting instrument to dip the pin once for every microarray spot that is to be printed.

Pins that take up sufficient target material to form dozens or hundreds of spots after one dip into the target liquid are also available. One type of pin is formed from a hollow cylindrical tube with an axial slot cut in the tip. This pin draws up sample liquid into the tube and slot by capillary action, and deposits it in much smaller amounts onto the substrate by capillary action upon contact with the microarray substrate. The uptake volume of the pin is sufficient to form dozens of spots by subsequent contact with other microarray substrates in the batch being processed.

Another type of multi-spot dispensing pins is a solid or two-piece pin, with a gap or slot at the tip. This type of pin draws fluid into the gap or slot by capillary action, and deposits a smaller amount onto the substrate by the inertia of the fluid when the pin is rapidly decelerated by lightly tapping it on the substrate. Again, the amount dispensed to form a spot is small compared to the sample uptake volume, so that each dip of the pin into sample liquid takes up enough sample to form dozens of spots.

Yet another type of multi-spot dispensing pin is solid, with a pyramidal taper at a tip that ends in a small, square flat. An even smaller slot is cut across the tip, providing a reservoir for sample liquid. The tip of the pin is then squeezed or bent slightly to bring the two segments of the slotted tip closer together.

In use, these slotted pins are again dipped into sample liquid, so that a fraction of a microliter of the sample is taken up into the slot by capillary action. The specific geometry and material of the pin also causes a very small amount of the bolus of liquid in the slot to wick out onto the two segments of the split pin tip. Then the fluid on the tip of the pin is brought into contact with the microarray substrate where surface energy attracts the fluid on the tip and forms a spot.

These microarray spotting dispensers, whether pins or ink-jet type, are generally mounted in a "printhead" in the spotting instrument. The printhead is typically a solid metal block which holds the dispensers and locates them precisely in three dimensions to facilitate accurate spot placement. The spotting instrument has a processor and positioning system to move the printhead with respect to the source plates of sample liquid, the substrates to be spotted, and the dispenser washing mechanism. Spotting instruments may move the printhead or the substrates and plates in any combination to facilitate the printing motions.

The printhead locates the dispensers on either 4.5 or 9.0 mm center spacing, for example, corresponding to spacing between wells in sample plates. Pin-type printheads are available with between 4 and 64 holes, accommodating between 4 and 64 pins, and ink-jet printheads are available with up to eight dispensers.

The precise location of the spotting dispensers with respect to other features in the spotting instrument should be well-known, with precision of at least a few tens of microns. The dispensers should be precisely centered in each well of the sample plate when taking up sample, as the plate wells are usually of a "v-bottom" type to maximize the ability to take up small volumes. Also, the dispenser washing/drying mechanism generally requires the dispenser to be placed into the centers of holes, the holes being about 1.25 to 2 times the dispenser diameter. Air drawn through these holes dries the dispensers and the dispensers must be well-centered in the holes to provide uniform drying and to prevent collisions with the sides of the holes. The locations of the dispensers with respect to the substrates should be known to a few tens of microns to allow downstream processing of the microarrays (e.g., scanning & quantitation of the scanned images) to be performed with precise knowledge of where the spots are located in the image field.

Spotting instruments are therefore calibrated, i.e., manipulated to cause the printhead and dispensers to move to various sample uptake, washing/drying, and printing positions, where the precision of its location is judged by a technician or some other sensing means external to the instrument, and the instrument control coordinates that correspond to each calibration location are recorded. The recorded calibration locations are utilized by the instrument controller to calibrate all dispenser positioning to be correct for each particular instrument. This calibration process removes the effects of unit-to-unit mechanical or dimensional control tolerances on the dispensers, the printhead, the sample plate holders, the substrate holders, the washer/dryer components, the motion-control mechanism, etc. A skilled technician or engineer is generally required to perform such calibration. The operation can be difficult because the instrument can be damaged easily when performing the motions before calibration is complete and also because judgment of positional accuracy based on magnified visual feedback is often required.

The printhead and dispensers have frequent cleaning and maintenance. Pins need periodic cleaning outside of the instrument. Pins and ink-jet dispensers need to be replaced if they are damaged due to accidental mechanical contact. Unintended spilling, splashing, or spraying of any liquid onto the printhead may also necessitate removing and cleaning of the printhead, especially pin-type printheads which rely on a low-friction slip-fit between the pins and the printhead.

Known mounting mechanism for printheads typically consist of two threaded holes in a nominally flat surface on one side of the printhead and screws that mate with the threaded holes and extend into clearance holes in a printhead mounting bracket on the instrument. When the printhead is removed and replaced, the location and angular tolerances allowed by this type of mounting system are typically 100 to 300 µm and 1 to 3 degrees of angle. The angle of the printhead is important because the dispensers typically protrude between 10 mm and 30 mm from the bottom of the printhead, and angular misalignment of the printhead results in displacements of the dispenser tips.

Another known printhead mount utilizes a locating pin permanently affixed to the printhead, with the axis of the locating pin axis being along the z-axis of the instrument (perpendicular to the surface on which the liquid is dispensed). The pin is held in a bayonet-type latching mechanism in the bracket. The bayonet latching mechanism provides a positive, repeatable location in the z axis by the action of a spring pressing a cross pin into a slot in the bracket mount. The x-axis position and y-axis position are less well controlled, however, due to the clearance between the printhead's bayonet pin and the bracket's socket required for the slip-fit of insertion. θx and θy are likewise not well-controlled due to the radial clearance in the bayonet connection.

The θz position is determined in the bayonet connection by a mechanical stop that is at a small radius (<10 mm) from the axis of the locating pin. Small angular misalignments cause relatively large displacements of the dispensers because the dispensers are located at a radius of about 25–50 mm from the center of the bayonet pin. The precision of this angular stop is limited to a few milliradians, limiting the precision of the x-y location of the dispensing pins to several tens of microns. Because the locating force is provided by a spring rather than the much higher forces delivered by screws, hysteresis of positioning caused by friction is not overcome by this mechanism.

SUMMARY OF THE INVENTION

It would be useful and desirable to be able to remove the printhead from the bracket of the spotting instrument for cleaning or maintenance, and then to be able to replace the printhead (that same printhead or a different one) on the instrument in exactly the same location, with a precision of several microns in the three translational degrees of freedom (x, y, and z) and with precision in the three angular degrees of freedom (θx, θy, and θz).

The present invention includes a printhead mounting system for a device that dispenses many small drops of liquid (on the order of nanoliters) on a workpiece at the same time, and particularly in a microarray spotting instrument for hybridization in which the liquid is dispensed into wells. The mounting system positively locates the printhead with respect to the instrument and to workpieces in six degrees of freedom with high repeatability when the printhead is removed and replaced. The system can be used with different types of pins or other dispensers for use in providing liquids to a surface.

In an embodiment of the present invention, a printhead is mounted to a printhead bracket with a semi-kinematic mount. Between the printhead and bracket are ball mounts, preferably hemispheres mounted on the printhead and for extending into openings in the bracket. Alternatively, some or all of the ball mounts could be located on the bracket. For the component that has a ball mount, the other component has openings for receiving pins that extend into that component and contact the ball mount at point contacts. In one embodiment, there are three sets of parallel pins, one for each ball mount, with a first pair of pins in one direction and second and third pairs of pins perpendicular to the first pair of pins and parallel to each other. Other mounts are possible, such as other semi-kinematic mounts, such as balls located in channels or grooves.

The system of the present invention allows the printhead to be mounted to the bracket with repeatability and tolerance of less than 50 microns in each translational direction and/or 5 milliradian, and more preferably less than 2 microns in each translational direction and/or 5 milliradian, thus avoiding the need for calibration with each mounting. While described for use with a microarray spotter, the system can be used with other liquid dispensing applications where there is a printhead for holding dispensers for providing many small drops of liquid on a workpiece. Other features and advantages become apparent from the following detailed description, drawings, and claims.

DETAILED DESCRIPTION OF THE INVENTION

This invention provides a printhead mount that positively locates a printhead in six degrees of freedom with repeatability of as good at 2 microns or less in the translational directions each time the printhead is removed and replaced. The invention preferably utilizes a semi-kinematic mounting system, and more preferably uses a mounting system with three ball mounts, with each ball mount locating itself between two parallel dowel pins when the printhead is installed on its bracket. Other mounts that constrain in six degrees of freedom without overconstraining could alternatively be used.

Figure 1:
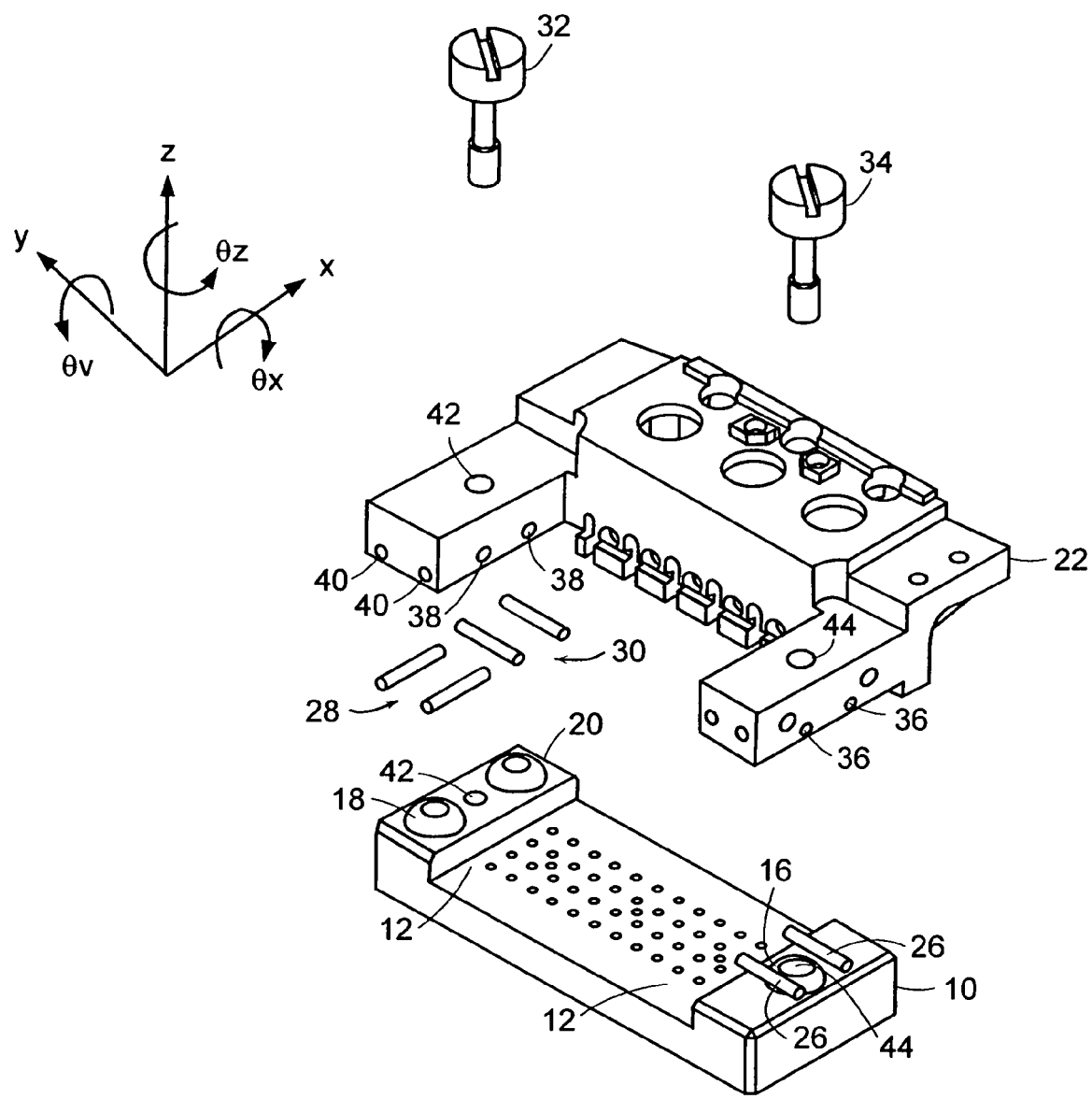
FIG. 1 is an exploded view of an embodiment of the present invention.

Referring to FIG. 1, in the embodiment described here, a printhead 10 is a modified version of a commercially available Telechem Stealth 48 printhead (available from Telechem International, Inc., Sunnyvale, Calif.). This commercial printhead is made of brass and is approximately 32 mm (x) by 83 mm (y) by 13 mm (z). The printhead has a region of dispenser pin holes 12; in this case, the region has 48 openings for dispensers and covers an area of approximately 13 mm (x) by 50 mm (y). U.S. Pat. No. 6,101,946, which is incorporated herein by reference, shows a view of a pins in a printhead (also referred to as a "holder").

Three ball mounts 16, 18, and 20 are rigidly attached to printhead 10, for example, by an interference fit in a hole or with an adhesive. Ball mounts 16, 18, and 20 are approximately hemispherical, e.g., 9.5 mm diameter and made of stainless steel, with a through-hole in the center and a flat surface perpendicular to the through hole. An example of such mounts is a #10 male spherical washer, available from Fasteners & Metal Products Corp., Waltham, Mass. Spherical surfaces of the ball mounts 16, 18, and 20 are exposed on printhead 10 and protrude above a top surface of printhead 10 by several millimeters.

The spacing between ball mounts 18 and 20 in the x-direction is wider than the region of openings in the printhead in the x-direction, which is 13 mm in the example above, and the spacing between ball mounts 16 and 20 in the y-direction is wider than the region of openings in the printhead in the y-direction, which is 50 mm in the example above. With such geometry, small locational errors at any ball mount cause smaller errors at the dispenser pin holes due to a leverage effect.

Figure 2:
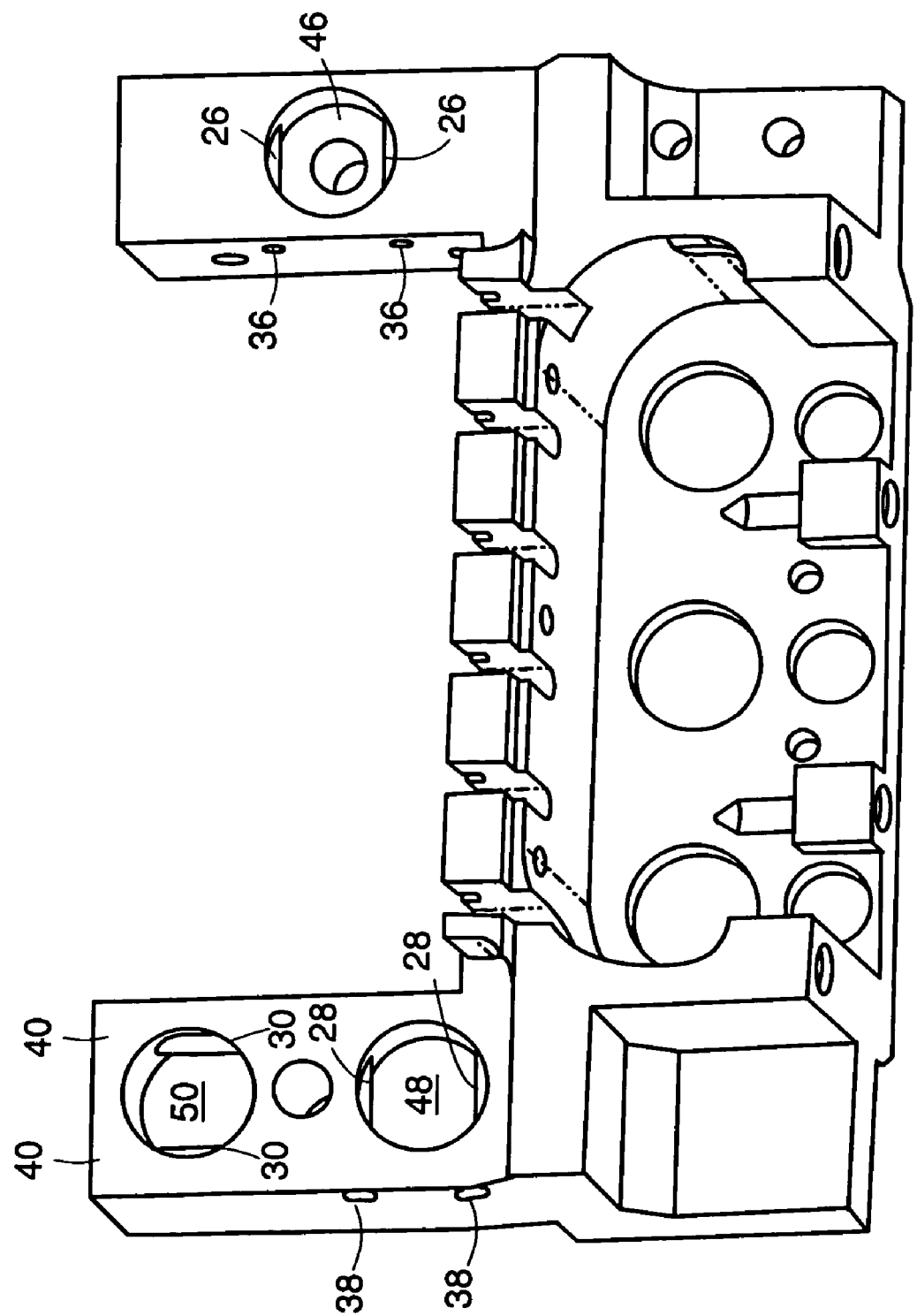
FIG. 2 is a bottom view of a printhead bracket.

Referring also to FIG. 1, a printhead bracket 22 is fitted with three pairs of dowel pins 26, 28, and 30, one pair to mate with each of the respective three ball mounts 16, 18, and 20. The dowel pins in FIG. 1 are shown in an exploded configuration; when assembled they are pressed into the three respective pairs of dowel pin holes 36, 38, and 40 in printhead bracket 22 as shown in FIG. 2. Dowel pins 26, 28, and 30 are spaced on 9.5 mm centers and are 3 mm diameter, so the spacing between their inner surfaces is about 6.5 mm. Two of the dowel pin pairs are oriented with their axes in the y-direction, and one pair is oriented in the x-direction.

Figure 3:
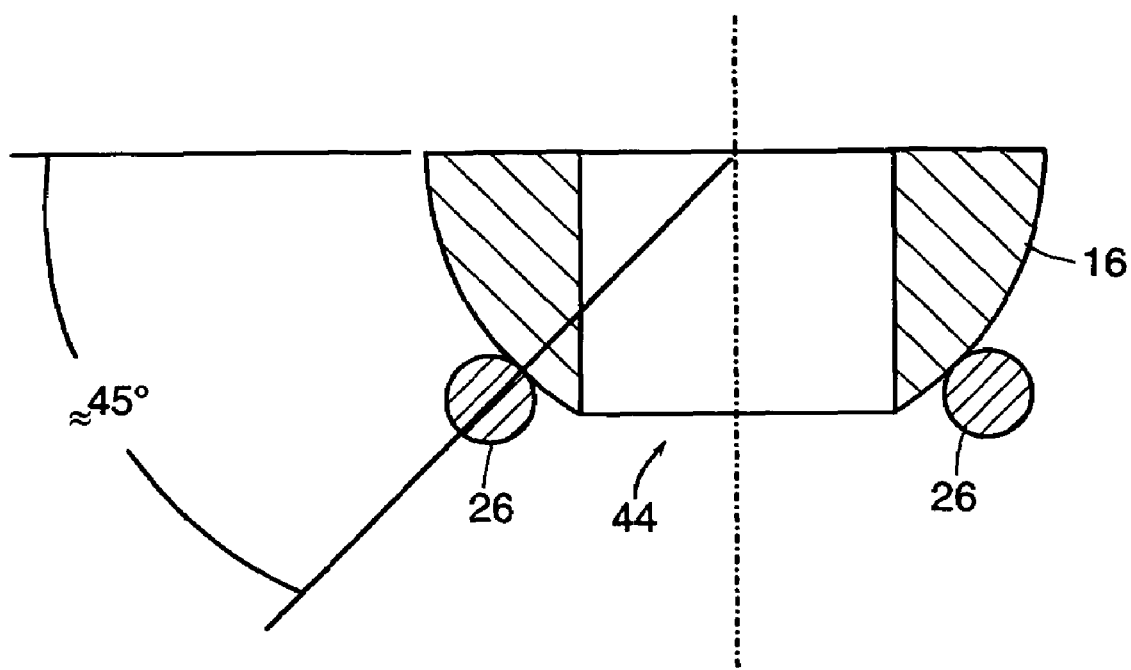
FIG. 3 is a cross-sectional view of a ball mount and pins.

When printhead 10 is brought into contact with the printhead bracket 22, each ball mount 16, 18, and 20 fits in a ball mount clearance hole 46, 48, and 50 (FIG. 2) between a pair of dowel pins. There are thus six points of contact, two at each ball mount. FIG. 3 shows one ball mount 16 and the sets of dowel pins 26 as illustrative, making two point contacts. The six points of contact constrain the position of the printhead with respect to the bracket in all six degrees of freedom. The mounting is thus not over-constrained; it accommodates locational tolerances on the ball mounts and the pins without inducing interferences in the mounting.

The mounting that is described here is referred to as semi-kinematic design. Other types of semi-kinematic mounting systems include systems with balls extending away from one plate and resting in sockets or in V-shaped channels in another plate. Such semi-kinematic mounts are shown and described, for example, in Yoder, "*Design and Mountings of Prisms and Small Mirrors and Optical Instruments*, SPIE—The International Society for Optical Engineering, 1998, Chapter 2, which describes a semi-kinematic mount as one with six constraints, each of which has a finite but small area to distribute force and minimize contact stress, and one that does not overconstrain. As indicated in Yoder, the use of kinematic and semi-kinematic mounts are known in the optical field for positioning prisms and mirrors.

The contact points should be with hard materials, such as hardened stainless steel. The use of hard materials at the mounting points is desirable so that the components can withstand contact stresses induced by printhead attachment and by instrument operation without deforming.

The mount is held together, printhead to printhead bracket, with two printhead mounting screws 32 and 34. These screws 32 and 34 pass through mounting screw clearance holes 42 and 44 in printhead bracket 22 and are engaged by threaded holes 42 and 44 in printhead 10. Screws 32 and 34 are preferably captive to bracket 22 and may be of the thumbscrew or other tool-free variety for ease of use. One of the mounting screws passes through hole 44 in ball mount 16, while the other screw passes through hole 42 between the other two ball mounts 18 and 20. This arrangement minimizes the effect of clamping forces from deforming the printhead and causing micron-level displacement of the dispenser tips. While only one of the ball mounts receives a screw, the other ball mounts may be provided with openings in order to maintain identical parts, or ball mounts can be provided without openings.

The mounts preferably surround the pattern of dispensers in the printhead. With such geometry, small locational errors at any ball mount cause smaller errors at the dispenser pin holes due to a leverage effect.

The repeatability is preferably less than 50 microns along the translational axes and 5 mrad in the rotational directions. It has been found that a printhead mount constructed as described above exhibits positioning repeatability of ≦2 µm in all three translational axes, measured by a 1 µm resolution electronic dial indicator. 2 µm displacement projected over the lever arms of the spacing between the mounting points translates to ≈0.13 mrad in θy and 0.03 mrad in θx.

In initial assembly, bracket 22 is mounted to a spotter's motion control system by mounts that allow the θx, θy, and θz angles to be adjusted. This adjustment is done with a simple fixture that aligns the mating surfaces of the three pairs of dowel pins to three fixtured ball mounts, where the fixture locates the ball mounts precisely with respect to the instrument's platen surface where the microarray substrates are to be located. Thereafter, the printhead can be removed and replaced without further calibration because of the level of accuracy of the mounting.

While an embodiment of the present invention has been described, it should be apparent that modifications can be made without departing from the scope of the present invention as defined by the appended claims. For example, all the dimensions that have been given are illustrative and based on specific components that were used, although other components with other dimensions could be used. A certain type of printhead has been described here as the base on which the mounting system was provided, but other shapes and configurations could be used as long as they hold dispensers for dispensing liquids. While certain components have been described as being on the printhead or the bracket, components could be reversed so that certain components shown on the printhead could be on the bracket and vice versa; for example, one, two, or three ball mounts could be on the bracket, with a respective two, one, or zero ball mounts on the printhead. The printhead can be for use with any type of dispensers or pins for dispensing small quantities of liquid at the same time. As indicated above, such known members for providing liquids include ink-jet-like dispensers with liquid dispensed through static pressure or a piezoelectric squeezing pulse, or dispenser pins that may be solid, flat tipped, cylindrically hollow, slotted, two-piece, pyramid-tapered at the tip with a slot, or some combination of these. The printhead and bracket can be used with generally known three-dimensional position controllers under control of a computer or other processor.

What is claimed is:

1. A liquid dispensing system for dispensing liquid drops on the order of nanoliter quantities with a number of dispensers arranged in parallel for dispensing liquid on a surface at the same time, the dispensing system including a printhead for holding the liquid dispensers, a bracket for removable connection to the printhead, and a semi-kinematic mounting system between the printhead and the bracket, wherein the mounting system includes three hardened ball mounts rigidly mounted on one or both of the bracket and printhead, wherein each of the ball mounts contacts two linear hardened dowel pins to constrain the printhead with respect to the bracket in six degrees of freedom, such that if the ball mount is on one of the bracket or printhead, the dowel pins fit in dowel pin holes in the other of the printhead or the bracket, wherein one set of the dowel pins is substantially orthogonal to at least one of the other two sets of dowel pins, wherein, after initial placement on the bracket, the printhead can be removed and replaced without requiring further calibration.

2. The dispensing system of claim 1, wherein the system includes a microarray spotter.

3. The system of claim 1, wherein the printhead has a region with openings for dispensers, wherein the ball mounts surround the region.

4. The system of claim 3, wherein the region has openings along an x-direction and a y-direction, and wherein the spacing between the mounts in the x-direction and the y-direction is larger than the dimensions of the region along the x-direction and the y-direction.

5. The system of claim 2, wherein positional repeatability error from subsequent mounting and replacing is less than 50 µm and/or 5 milliradian.

6. The system of claim 5, wherein the positional repeatability error from subsequent mounting and replacing is less than 2 microns and/or 0.13 milliradian.

7. The system of claim 1, wherein at least one of the mounts has an opening for receiving a screw passing between the bracket to the printhead.

8. The system of claim 1, further comprising a positioning system connected to the bracket, and a controller for controlling the positioning system to move along three coordinate axes.

9. The system of claim 2, further comprising a positioning system connected to the bracket, and a controller for controlling the positioning system to move along three coordinate axes.

10. The system of claim 1, wherein positional repeatability error from subsequent mounting and replacing is less than 50 µm and/or 5 milliradian.

11. The system of claim 10, wherein the positional repeatability error from subsequent mounting and replacing is less than 2 microns and/or 0.13 milliradian.

12. A microarray spotter including a printhead, a bracket, and a semi-kinematic mounting system between the printhead and the bracket, the mounting system being sufficiently precise to provide repeatable accuracy within 50 microns along three translational axes, wherein the mounting system includes three hardened ball mounts rigidly mounted on one or both of the bracket and printhead, wherein each of the ball mounts contacts two linear, hardened dowel pins fitted in one or both of the bracket and printhead to constrain the printhead with respect to the bracket in six degrees of freedom, wherein, after initial placement on the bracket, the printhead can be removed and replaced without requiring further calibration.

13. The microarray spotter of claim 12, wherein the repeatable accuracy is within 2 microns along the three translational axes.

14. A microarray spotter including a printhead, a bracket, and a semi-kinematic mounting system between the printhead and the bracket, the printhead holding dispensers for dispensing liquid onto an array with wells, wherein said dispensers are no more than about 9 mm apart, the mounting system being a including three ball mounts in one of the printhead or bracket, each ball mount contacting two dowel pins in the other of the printhead or bracket to constrain the printhead with respect to the bracket in six degrees of freedom to provide sufficient locational accuracy so that the printhead can be repeatedly removed and replaced from the bracket without requiring further calibration.

15. The microarray spotter of claim 14, wherein the dispensers are no more than about 4.5 mm apart.

* * * * *